(12) United States Patent
Roychowdhury et al.

(10) Patent No.: US 7,491,812 B1
(45) Date of Patent: Feb. 17, 2009

(54) COPPER-INDUCIBLE PROMOTER SYSTEM

(75) Inventors: Hiranya S. Roychowdhury, Las Cruces, NM (US); Maria Ordaz, El Paso, TX (US); Kristina Dominguez-Trujillo, Las Cruces, NM (US); Glenn D. Kuehn, Las Cruces, NM (US)

(73) Assignee: Arrowhead Center, Inc., Las Cruces, NM (US)

( * ) Notice: Subject to any disclaimer, the term of this patent is extended or adjusted under 35 U.S.C. 154(b) by 94 days.

(21) Appl. No.: 11/120,009

(22) Filed: May 2, 2005

Related U.S. Application Data

(60) Provisional application No. 60/567,232, filed on Apr. 30, 2004.

(51) Int. Cl.
*C12N 15/11* (2006.01)
*C12N 15/00* (2006.01)
*C12N 15/66* (2006.01)

(52) U.S. Cl. .................. 536/24.1; 536/24.2; 435/320.1; 435/91.4; 435/91.41

(58) Field of Classification Search ................. None
See application file for complete search history.

(56) References Cited

U.S. PATENT DOCUMENTS

| | | |
|---|---|---|
| 6,004,779 A | 12/1999 | Bradley et al. |
| 6,365,409 B1 | 4/2002 | Bradley et al. |
| 6,531,289 B1 | 3/2003 | Bradley et al. |
| 6,576,469 B1 | 6/2003 | Struhl et al. |
| 6,759,529 B1 * | 7/2004 | Misra et al. ............ 536/24.1 |
| 2004/0018625 A1 | 1/2004 | Struhl et al. |

OTHER PUBLICATIONS

Chan et al, Delayed Secondary Glucocorticoid Response Elements, JBC, 1991, vol. 266(33), pp. 22634-22644.*
Mett et al, Copper-controlled gene expression system for whole plants, PNAS, 1993, vol. 90, pp. 4567-4571.*
Promega, pGEM-3Zf(-) vector, downloaded Jan. 21, 2007.*
Mett et al , A system for tissue- specific copper-controllable gene expression in transgenic plants: nodule-specific antisense of asparate aminotransferase-P2, Transgenic Research, 1996, vol. 5, pp. 105-113.*
DeFranco et al, Two Different Factors Act Separately or Together To Specify Functionally Distinct Activities at a Single Transcriptional Enhancer, MCB, 1986, vol. 6(4), pp. 993-1001.*
Nemer et al, Structure, SPatial and Temporal Expression of Two Sea Urchin Metallothionein Genes, SpMTB1 and SpMTA. JBC, 1991 , vol. 266 (1), pp. 6586-6593.*
Mett, Vadim , et al., "Copper-controllable Gene Expression System for Whole Plants", *Proc. Natl. Acad. Sci. USA*, vol. 90, (May 1993),4567-4571.
Sambrook, J. , et al., "Text: Molecular Cloning—A Laboratory Manual", *3rd Edition, Cold Spring Harbor Laboratory Press*, Cold Spring Harbor, New York, Index pages,(2001),v-xx.

* cited by examiner

*Primary Examiner*—Maria Marvich
(74) *Attorney, Agent, or Firm*—Vidal A. Oaxaca; Janeen Vilven; Peacock Myers, P.C.

(57) ABSTRACT

The present invention comprises a copper-inducible promoter system of yeast for the controlled expression of recombinant genes. The invention comprises a promoter element comprising at least two tandemly-repeated MRE sequences and a minimal TATA element from the 35S-promoter of the cauliflower mosaic virus.

8 Claims, No Drawings

US 7,491,812 B1

COPPER-INDUCIBLE PROMOTER SYSTEM

CROSS-REFERENCE TO RELATED APPLICATIONS

This application claims the benefit of the filing of U.S. Provisional Patent Application Ser. No. 60/567,232, entitled "Copper-Inducible Promoter System", filed Apr. 30, 2004, and the specification of that application is incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of the National Institutes of Health Grant No. 3 S06 GM08136.29.

BACKGROUND OF THE INVENTION

1. Field of the Invention (Technical Field)

The present invention relates to an improved copper-inducible promoter system in yeast for the controlled expression of recombinant genes.

2. Background Art

Inducible promoters that can provide precise temporal control over transgene expression are widely used to investigate recombinant gene functions. The copper-inducible gene expression system from Saccharomyces cerevisiae was first successfully introduced into tobacco by Mett et al. (Proc. Natl. Acad. Sci. USA 90:4567-4571 (1993)), which is incorporated herein by reference. This system consists of two elements: (i) the yeast activating copper-element (ace I) gene encoding copper-responsive transcription factor ACE1, and (ii) the metal responsive element (MRE) containing ACE1-binding sites. When copper(II)-ion binds to transcription factor ACE1, the ion alters the protein's conformation thereby promoting binding of the protein to the MRE, which then triggers the transcription of a target gene ligated downstream from the MRE.

The benefit of the copper-inducible system is that it does not interfere with the normal physiology of the affected organism. However, the system has not been consistently successful. Therefore, there is a need for an effective copper-inducible promoter system.

BRIEF SUMMARY OF THE INVENTION

The present invention provides a promoter element comprising two tandemly-repeated MRE sequences. The promoter element preferably comprises a TATA element from the 35S-promoter of the cauliflower mosaic virus. The MRE sequences are preferably placed in a vector, preferably a pGEM3zf vector between the EcoRI and BamHI sites of the vector. The promoter element preferably comprises SEQ ID NO:5.

The present invention also provides a promoter element comprising two tandemly-repeated MRE sequences, and a TATA element from the 35S-promoter of the cauliflower mosaic virus placed immediately downstream of said MRE sequences, said MRE sequences and said TATA element being disposed in a PGEM3zf vector between the EcoRI and BamHI sites of said vector.

The present invention also provides a method for constructing a promoter element comprising annealing two primers to form a MRE binding site, tandemly repeating the MRE binding site to form a duplex, and ligating a sequence representing a "TATA" box of the 35S CaMV promoter immediately downstream from the duplex.

The method preferably further comprises cloning the duplex into a vector. The vector of the method preferably comprises a pGEM3zf vector In the method, forming the duplex preferably comprises cloning the duplex into a pGEM3zf vector between an EcoRI site and a SacI site to form a construct, digesting the construct with SacI and BamHI, religating the construct, performing reciprocal digestion with EcoRI and BamHI, and religating the construct so that the duplex is placed between the EcoRI and BamHI sites of the pGEM3zf vector.

DETAILED DESCRIPTION OF THE INVENTION

The present invention relates to a copper-inducible promoter system of yeast for the controlled expression of recombinant genes. An embodiment of the present invention comprises a promoter element comprising at least two tandemly-repeated metal responsive element ("MRE") sequences (comprising ACE1 binding sites) preferably followed by a promoter domain, preferably a minimal TATA element from the 35S-promoter of the cauliflower mosaic virus ("CaMV"), and includes the method for constructing the promoter element.

In practicing the present invention, conventional techniques known in the field in microbiology, molecular biology, and recombinant DNA may be utilized such as those described in, but not limited to, Molecular Cloning: a Laboratory Manual, J. Sambrook, E. F. Fritsch, T. Maniatis, incorporated herein by reference.

In yet another embodiment, an ACE1 Binding Site (from Saccharomyces cerevisiae) is constructed by annealing the following primers: 5'-MTTCAGCGATGCGTCTTTTC-CGCT GMCCGTTCCAGCAAAAMGACTAGAGCT-3' (SEQ ID NO:1); and 5'-CTAGTCTTTTTT GCTGGAACG GTTCAGCGGAAAAGACGCATCGCTG-3' (SEQ ID NO:2). The annealed duplex is preferably cloned into a pGEM3zf vector between the EcoRI and SacI sites. Digestion of the pGEM3zf vector containing the annealed primers is then preferably performed using SacI and BamHI, and the ends of the sequence containing the primers are preferably polished and religated. Reciprocal digestion with EcoRI and BamHI, blunting, and religating is then performed to form a tandemly duplicated sequence of the ACE1 Binding Site, each sequence being approximately fifty nucleotides long, herein designated ABS2, placed between the EcoRI and BamHI sites of the modified vector pGEM3zf.

Preferably, the two oligonucleotides; 5'-GGGCAAGAC-CCTTCCTCTATA TMGGMGTTCATTTCATTTG-GAGAGGACACGCTG-3' (SEQ ID NO:3); and 5'-GATC-CAGCGT GTCCTCTCCAMTGAAATGAACTTCCTTAT-ATAGAGGAAGGGTC TTGCCC-3' (SEQ ID NO:4), representing the minimal "TATA" box of the 35S CaMV promoter, are annealed and ligated immediately downstream from the ABS2 sequence to form a final construct. The final construct is designated herein as ABS2TA and comprises the sequence 5'-GMTTCAGCGATGCGTCTTTTCCGCTGAACCGTT-CCAGCAAAAAAGACTAGG ATCA ATTCAGCGAT-GCGTCTTTTCCGCTGMCCGTTCCAGCAAAAAAGA-CTAGGATCGGGCAAG ACCCTTCCTCTATATMG-GMGTTCATTTCATTTGGAGAGGACACGCTGGATCC-3' (SEQ ID NO:5). The 170 base pair ABS2TA element comprises 5'-EcoRI AND 3'-BamHI ends.

A gene of interest is then cloned between the SalI and HindIII sites downstream from the ABS2TA promoter in the ABS2TA/pGEM3zf vector. For example, the 3.5 kb beta galactosidase gene, used as the reporter, is cloned between the SalI and HindIII sites downstream from the ABS2TA promoter in the ABS2TA/pGEM3zf vector.

A promoter according to one of the embodiments of the present invention is utilized to control gene traits in, for example, yeast and plants.

EXAMPLE

The promoter system and methods of the present invention as described above were carried out and tested as follows:

1. An ACE1 Binding Site of *Saccharomyces cerevisiae* was constructed by annealing the following primers: 5'-AAT-TCAGCGATGCGTCTTTTCCGCTGAACCGTT CCAG-CAA AAAAGACTAGAGCT-3'; and 5'-CTAGTCTTTTT-TGCTGGAACGGTTCAGCGGAAAAGACGCA TCGC-TG-3'. The annealed duplex was cloned into a pGEM3zf vector between the EcoRI and SacI sites. Digestion of the vector was performed with SacI and BamHI, the ends of the sequence containing the duplex polished and relegated. Reciprocal digestion with EcoRI and BamHI, blunting, and religating created a tandemly duplicated sequence of the ACE1 Binding Site ("ABS2"), situated between the EcoRI and BamHI sites of the modified vector pGEM3zf.

2. Two oligonucleotides, 5'-GGGCMGACCCTTCCTC-TATATMGGMGTTCATTTCA TTTGGAGAGGA-CACGCG-3' and 5'-GATCCAGCGTGTCCTCTCCAAAT-GAAATGMCTTCC TTATATAGAGGMGGGTCTTGCCC-3', representing the minimal "TATA" box of the 35S promoter, were annealed and ligated immediately downstream from the ABS2 sequence. The 170 base pair final construct, ABS2TA, comprised the sequence 5'-GAAT-TCAGCGAT GCGTCTTTTCCGC TGMCCGTTCCAG-CAAAAAGACTAGG ATCMTTCAGCGATGCGTC TTTTCCGCT GMCCGTTCCAGCAAAAAAGACTAG-GATCGGGCAAGACCCTTCCTCTATA TAAGGAAGT-TCATTTCATTTGGAGAGGACACGCTGGATCC-3' and had 5'-EcoRI AND 3'-BamHI ends. ABS2TA was tested for its in vivo copper responsive expression in the homologous host *S. cerevisiae*, using the beta galactosidase gene.

3. The 3.5 kb beta galactosidase gene, used as the reporter, was cloned between the SalI and HindIII sites downstream from the ABS2TA promoter in the ABS2TA/pGEM3zf vector. Subsequently the ABS2TA-beta Galactosidase insert, between EcoRI and HindIII, was transferred to the multiple cloning site of pYES2 vector (Invitrogen) for yeast expression studies.

4. The expression of the promoter construct of Mett et al. was tested in the homologous host, *S. cerevisiae*, using the reporter gene for β-galactosidase. It exhibited high background and low inducibility in both the absence and presence of exogenous $Cu^{2+}$, respectively.

A promoter as in this Example in *S. cerevisiae* demonstrated vastly improved regulatory properties with respect to inducibility by $Cu^{2+}$. ABS2TA demonstrated increasing and linear inducibility from approximately 0.5 to 600 µM $Cu^{2+}$. Maximally-induced levels of β-galactosidase were approximately >60 times higher than uninduced levels. Leakiness of ABS2TA in the absence of $Cu^{2+}$ was approximately <1.7% of induced levels. Inducibility with $Cu^{2+}$ at all stages of the yeast growth cycle was rapid and linear, showing enhanced levels of β-galactosidase within approximately 20 min of exposure to $Cu^{2+}$. Maximum induction by $Cu^{2+}$ was 410 times stronger by ABS2 promoter than by the promoter of Mett et al.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above, and of the corresponding application(s), are hereby incorporated by reference.

What is claimed is:

1. An isolated promoter comprising not more than one MRE duplex consisting of two tandemly-repeated MRE sequences wherein each MRE sequence comprises an ACE1 binding site.

2. The promoter of claim 1 further comprising a minimal TATA element from a 35S-promoter of a cauliflower mosaic virus.

3. The promoter of claim 2 wherein said promoter is inserted into a vector.

4. The promoter of claim 3 wherein said vector comprises pGEM3zf.

5. The promoter of claim 4 wherein said promoter is placed between the EcoRI and BamHI sites of pGEM3zf.

6. The promoter of claim 2 comprising SEQ ID NO:5.

7. The promoter of claim 2 consisting essentially of SEQ ID NO:5.

8. An isolated promoter comprising not more than one MRE duplex consisting of two tandemly-repeated MRE sequences wherein each MRE sequence comprises an ACE1 binding site; and
   a minimal TATA element from a 35S-promoter of a cauliflower mosaic virus, said TATA element placed immediately downstream of said MRE duplex; and
   wherein said MRE duplex and said TATA element are disposed in a PGEM3zf vector between the EcoRI and BamHI sites of said vector.

* * * * *

SEQUENCE LISTING

```
<160> NUMBER OF SEQ ID NOS: 5

<210> SEQ ID NO 1
<211> LENGTH: 54
<212> TYPE: DNA
<213> ORGANISM: Artificial Sequence
<220> FEATURE:
<223> OTHER INFORMATION: ACE1 Primer 1

<400> SEQUENCE: 1
aattcagcga tgcgtctttt ccgctgaacc gttccagcaa aaaagactag agct         54

<210> SEQ ID NO 2
<211> LENGTH: 46
<212> TYPE: DNA
<213> ORGANISM: Artificial Sequence
<220> FEATURE:
<223> OTHER INFORMATION: ACE1 Primer 2

<400> SEQUENCE: 2
ctagtctttt ttgctggaac ggttcagcgg aaaagacgca tcgctg                  46
```

<210> SEQ ID NO 3
<211> LENGTH: 56
<212> TYPE: DNA
<213> ORGANISM: Artificial Sequence
<220> FEATURE:
<223> OTHER INFORMATION: 35S Oligonucleotide 1

<400> SEQUENCE: 3
gggcaagacc cttcctctat ataaggaagt tcatttcatt tggagaggac acgctg     56

<210> SEQ ID NO 4
<211> LENGTH: 60
<212> TYPE: DNA
<213> ORGANISM: Artificial Sequence
<220> FEATURE:
<223> OTHER INFORMATION: 35S Oligonucleotide 2

<400> SEQUENCE: 4
gatccagcgt gtcctctcca aatgaaatga acttccttat atagaggaag ggtcttgccc     60

<210> SEQ ID NO 5
<211> LENGTH: 170
<212> TYPE: DNA
<213> ORGANISM: Artificial Sequence
<220> FEATURE:
<223> OTHER INFORMATION: ABS2TA

<400> SEQUENCE: 5
gaattcagcg atgcgtcttt tccgctgaac cgttccagca aaaagacta ggatcaattc      60 agcgatgcgt cttttccgct gaaccgttcc agcaaaaaag actaggatcg ggcaagaccc    120
ttcctctata taaggaagtt catttcattt ggagaggaca cgctggatcc                170